US008530099B2

(12) United States Patent
Chen et al.

(10) Patent No.: US 8,530,099 B2
(45) Date of Patent: *Sep. 10, 2013

(54) MULTIFUNCTIONAL SULFONE/FLUORINATED ESTER SOLVENTS

(75) Inventors: Xudong Chen, Hockessin, DE (US); William L. Holstein, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/328,279

(22) Filed: Dec. 16, 2011

(65) Prior Publication Data

US 2012/0323036 A1 Dec. 20, 2012

Related U.S. Application Data

(63) Continuation of application No. 12/961,587, filed on Dec. 7, 2010, now Pat. No. 8,092,942.

(51) Int. Cl.
*H01M 6/16* (2006.01)
(52) U.S. Cl.
USPC .................. 429/340; 199/326; 199/332
(58) Field of Classification Search
USPC .................. 429/332, 340, 46, 199, 326
See application file for complete search history.

(56) References Cited

U.S. PATENT DOCUMENTS

| 5,561,232 | A | 10/1996 | Hao et al. |
| 5,659,062 | A | 8/1997 | Yokoyama et al. |
| 6,495,293 | B1 | 12/2002 | Arai et al. |
| 6,534,220 | B2 | 3/2003 | Garbe |
| 6,878,492 | B2 | 4/2005 | Takeuchi |
| 7,312,001 | B2 | 12/2007 | Kim |
| 2003/0190529 | A1 | 10/2003 | Kim et al. |
| 2004/0157133 | A1 | 8/2004 | Kim et al. |
| 2007/0148540 | A1 | 6/2007 | Chiga et al. |
| 2008/0131772 | A1 | 6/2008 | Jambunathan et al. |
| 2008/0145763 | A1 | 6/2008 | Koh et al. |
| 2011/0008684 | A1 | 1/2011 | Jeon |

FOREIGN PATENT DOCUMENTS

| JP | 4328915 B2 | 6/2009 |
| JP | 2011/071098 | 4/2011 |

OTHER PUBLICATIONS

Xu et al, Sulfone-Based Electrolytes for Lithium-Ion Batteries, Journal of the Electrochemical Society, 2002, A920-A926, 149 (7).
Romanovskiy et al., The Universal Solvent Extraction (UNEX) Process. I. Development of the UNEX Process Solvent for the Separation of Cesium, Strontium, and the Actinides From Acidic Radioactive Waste, Solvent Extraction and Ion Exchange, 19(1), 1-21 (2001).

*Primary Examiner* — Patrick Ryan
*Assistant Examiner* — Alex Usyatinsky

(57) ABSTRACT

Novel multifunctional sulfone/fluorinated ester compounds are described. These compounds may be useful as non-aqueous electrolyte solvents, specialty solvents, and starting materials and intermediates for synthesis of dyes, agricultural chemicals, and pharmaceuticals.

17 Claims, No Drawings

MULTIFUNCTIONAL SULFONE/FLUORINATED ESTER SOLVENTS

This application is a continuation of, and claims the benefit of, U.S. Ser. No. 12/961,587, filed Dec. 7, 2010, which is by this reference incorporated in its entirety as a part hereof for all purposes.

TECHNICAL FIELD

The invention relates to novel multifunctional sulfone/fluorinated ester compounds which are useful as nonaqueous solvents having excellent anti-oxidation properties.

BACKGROUND

Carbonate compounds are currently used as electrolyte solvents for non-aqueous batteries containing cathodes made from alkali metals, alkaline earth metals, or compounds comprising these metals, for example lithium ion batteries. Current lithium ion battery electrolyte solvents typically contain one or more linear carbonates, such as ethyl methyl carbonate, dimethyl carbonate, or diethylcarbonate; and a cyclic carbonate, such as ethylene carbonate. However, at battery voltages above 4.4 V these electrolyte solvents decompose resulting in a loss of battery performance. Additionally, there are safety concerns with the use of these electrolyte solvents because of their low boiling point and high flammability.

To overcome the limitations of commonly used non-aqueous electrolyte solvents, several new carbonate compounds have been developed. For example, Yokoyama et al., (U.S. Pat. No. 5,659,062) describe novel carbonate compounds given by the general formula $R^1CH_2O\text{—}CO\text{—}OCH_2R^2$, wherein $R^1$ represents a hydrogen atom, an alkyl group, or an alkyl group substituted with one or more halogen atoms, and $R^2$ represents an alkyl group having no hydrogen atom at the α-position thereof or an alkyl group substituted with one or more halogen atoms and having no hydrogen atom at the α-position thereof, with the proviso that $R^1$ is not identical to $R^2$. Additionally, various fluorinated ester electrolyte solvents have been described for use in lithium ion batteries (see for example, Nakamura et al. JP4328915B2).

Xu et al. (*J. Electrochem. Soc.* 149(7):A920-A926, 2002) have proposed the use of sulfone-based electrolytes, including fluorinated sulfones such as 3,3,3,-trifluoropropylmethyl sulfone, for lithium ion batteries.

However, the need exists for more electrolyte solvents, which are highly stable to oxidation and have a high boiling point, for use in non-aqueous battery systems, such as lithium ion batteries.

SUMMARY

The present invention addresses the above need by providing novel multifunctional sulfone/fluorinated ester compounds that may be useful as non-aqueous electrolyte solvents, as well as specialty solvents, and starting materials and intermediates for synthesis of dyes, agricultural chemicals, and pharmaceuticals.

Accordingly, in one embodiment, the invention provides a composition represented by the structure:

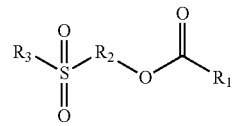

wherein $R_1$ is C1 to C4 fluoroalkyl; $R_2$ is C1 to C6 alkylene radical, optionally substituted with one or more ether oxygens; and $R_3$ is C1 to C6 alkyl, optionally substituted with one or more ether oxygens.

In another embodiment, the invention provides an electrochemical cell that includes the composition described above.

In another embodiment, the invention provides a process for forming a composition comprising the step of: combining, optionally in a solvent,

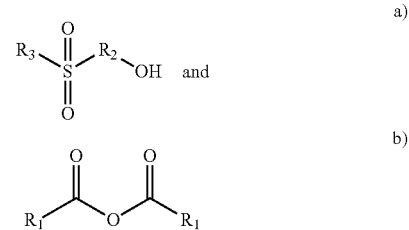

wherein $R_1$ is C1 to C4 fluoroalkyl; $R_2$ is C1 to C6 alkylene radical, optionally substituted with one or more ether oxygens; and $R_3$ is C1 to C6 alkyl, optionally substituted with one or more ether oxygens.

DETAILED DESCRIPTION

As used above and throughout the description of the invention, the following terms, unless otherwise indicated, shall be defined as follows:

The term "fluoroalkyl" refers to an alkyl group wherein one or more fluorine atoms have been substituted for hydrogen atoms.

The term "alkyl group" refers to a univalent group derived from a straight or branched chain alkane by removal of one hydrogen atom from any carbon atom.

The term "alkylene radical" refers to a chemical group derived functionally by removal of one hydrogen atom from any two carbon atoms of an alkyl group, e.g.,

The term "ether oxygen" refers to an oxygen atom that is part of an ether bond, wherein the oxygen atom is bound to two alkyl groups, e.g., R—O—R', where R may be the same as or different from R'.

The term "electrolyte composition" as used herein, refers to a chemical composition suitable for use as an electrolyte in an electrochemical cell. An electrolyte composition typically comprises at least one solvent and at least one electrolyte salt.

The term "electrolyte salt" as used herein, refers to an ionic salt that is at least partially soluble in the solvent of the electrolyte composition and that at least partially dissociates into ions in the solvent of the electrolyte composition to form a conductive electrolyte composition.

The term "anode" refers to the electrode of an electrochemical cell, at which oxidation occurs. In a galvanic cell, such as a battery, the anode is the negatively charged electrode.

The term "cathode" refers to the electrode of an electrochemical cell, at which reduction occurs. In a galvanic cell, such as a battery, the cathode is the positively charged electrode.

The term "lithium ion battery" refers to a type of rechargeable battery in which lithium ions move from the anode to the cathode during discharge, and from the cathode to the anode during charge.

Disclosed herein are novel multifunctional sulfone/fluorinated ester compounds that may be useful as electrolyte solvents for non-aqueous battery systems, such as lithium ion batteries, as well as specialty solvents and starting materials and intermediates for organic synthesis.

The multifunctional sulfone/fluorinated ester compounds disclosed herein are represented by the structure:

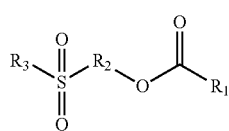

(1)

wherein $R_1$ is C1 to C4 fluoroalkyl; $R_2$ is C1 to C6 alkylene radical, optionally substituted with one or more ether oxygens; and $R_3$ is C1 to C6 alkyl, optionally substituted with one or more ether oxygens.

In one embodiment, the multifunctional sulfone/fluorinated ester compound is 2-(methylsulfonyl)ethyl 2,2,2-trifluoroacetate, wherein in structure (1) $R_1$ is $CF_3$, $R_2$ is $CH_2CH_2$, and $R_3$ is $CH_3$. In another embodiment, the multifunctional sulfone/fluorinated ester compound is 2-(methylsulfonyl)ethyl 2,2-difluoroacetate, wherein in structure (1) $R_1$ is $CF_2H$, $R_2$ is $CH_2CH_2$, and $R_3$ is $CH_3$.

These multifunctional sulfone/fluorinated ester compounds can be prepared by a process comprising: combining

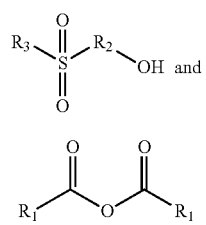

wherein $R_1$ is C1 to C4 fluoroalkyl; $R_2$ is C1 to C6 alkylene radical, optionally substituted with one or more ether oxygens; and $R_3$ is C1 to C6 alkyl, optionally substituted with one or more ether oxygens. The process may be carried out in an optional solvent. Suitable solvents are polar aprotic solvents, including, but not limited to, dichloromethane, chloroform, ether, and tetrahydrofuran. In one embodiment, the solvent is dichloromethane.

In one embodiment, the compound represented by structure (2) is 2-methylsulfonyl ethanol, wherein $R_2$ is $CH_2CH_2$, and $R_3$ is $CH_3$, and the compound represented by structure (3) is trifluoroacetic anhydride wherein each $R_1$ is $CF_3$, as described in detail in Example 1 herein. In another embodiment, the compound represented by structure (2) is 2-methylsulfonyl ethanol, wherein $R_2$ is $CH_2CH_2$, and $R_3$ is $CH_3$, and the compound represented by structure (3) is difluoroacetic anhydride wherein each $R_1$ is $CF_2H$, as described in detail in Example 2 herein.

The compounds represented by structures (2) and (3) may be combined in any suitable reaction vessel. Typically, the optional solvent, if used, is dried and the reaction is carried out in a dry box or under nitrogen protection to exclude moisture from the air. Reaction conditions for the process may vary. For example, reaction temperatures may vary depending on a number of factors such as the concentration of reactants, the stability of the product formed, reaction time and yield desired. Suitable temperatures range from 0° C. up to refluxing conditions. In some embodiments, the reaction is carried out at room temperature (i.e., approximately 20° C.).

The resulting mixture is mixed for a time sufficient for the formation of the multifunctional sulfone/fluorinated ester product, typically 0.5 to 1 hour. After this time, volatile components may be removed using methods known in the art, such as evaporation under vacuum. The product may be recovered and purified using standard methods such as vacuum distillation or column chromatography.

The multifunctional sulfone/fluorinated ester compounds disclosed herein may be used in various applications including, but not limited to, non-aqueous electrolyte solvents, specialty solvents, and starting materials and intermediates for synthesis of dyes, agricultural chemicals, and pharmaceuticals. The multifunctional sulfone/fluorinated ester compounds disclosed herein may be particularly useful as electrolyte solvents for non-aqueous batteries containing cathodes made from alkali metals, alkaline earth metals, or compounds comprising these metals, for example lithium ion batteries.

In one embodiment, the invention provides an electrolyte composition comprising at least one multifunctional sulfone/fluorinated ester compound as set forth in structure (1) and at least one electrolyte salt, wherein the electrolyte salt is at least partially soluble in the multifunctional sulfone/fluorinated ester compound at the desired operating temperature. The electrolyte composition may further comprise one or more co-solvents, and various additives known in the art, such as a surfactant. For example for a lithium ion battery, the electrolyte composition may comprise at least one co-solvent selected from ethyl methyl carbonate, dimethyl carbonate, diethyl carbonate, ethylene carbonate, propylene carbonate, vinylethylene carbonate, fluoroethylene carbonate, 2,2,2-trifluoroethyl carbonate, and methyl 2,2,3,3-tetrafluoropropyl carbonate.

The multifunctional sulfone/fluorinated ester compound as set forth in structure (1) and the co-solvent may be combined in various ratios depending on the desired properties of the electrolyte composition. Suitable combining ratios for any particular application can be readily determined by one skilled in the art using routine optimization. In one embodiment, the multifunctional sulfone/fluorinated ester compound comprises about 5% to about 60% of the solvent mixture. In another embodiment, the multifunctional sulfone/fluorinated ester compound comprises about 20% to about 40% of the solvent mixture. In another embodiment, the multifunctional sulfone/fluorinated ester compound comprises about 30% of the solvent mixture.

In one embodiment, the electrolyte composition comprises a mixture of 2-(methylsulfonyl)ethyl 2,2,2-trifluoroacetate and 2,2,3,3-tetrafluoropropyl carbonate or methyl 2,2,2-trifluoroethyl carbonate. In another embodiment, the electrolyte composition comprises a mixture of 2-(methylsulfonyl)ethyl 2,2-difluoroacetate and 2,2,3,3-tetrafluoropropyl carbonate or methyl 2,2,2-trifluoroethyl carbonate.

Suitable electrolyte salts for use in a lithium ion battery include, but are not limited to, lithium hexafluorophosphate, lithium bis(trifluoromethanesulfonyl)imide, lithium bis(perfluoroethanesulfonyl)imide, lithium tetrafluoroborate, lithium perchlorate, lithium hexafluoroarsenate, lithium trifluoromethanesulfonate, lithium tris(trifluoromethanesulfonyl)methide, lithium bis(oxalato)borate, $Li_2B_{12}F_{12-x}H_x$ where x is equal to 0 to 8, and mixtures of lithium fluoride and anion receptors such as $B(OC_6F_5)_3$. In one embodiment, the electrolyte salt is lithium hexafluorophosphate.

In another embodiment, the invention provides an electrochemical cell comprising a housing, an anode and a cathode disposed in the housing and in ionically conductive contact with one another, an electrolyte composition, as described above, providing an ionically conductive pathway between the anode and the cathode, and a porous separator between the anode and the cathode. The housing may be any suitable container to house the electrochemical cell components.

The anode and the cathode may be comprised of any suitable conducting material depending on the type of electrochemical cell. Suitable examples of anode materials include, but are not limited to, lithium metal, lithium metal alloys, aluminum, platinum, palladium, graphite, transition metal oxides, and lithiated tin oxide. Suitable examples of cathode materials include, but are not limited to, graphite, aluminum, platinum, palladium, electroactive transition metal oxides comprising lithium, indium tin oxide, and conducting polymers such as polypyrrole and polyvinylferrocene.

The porous separator serves to prevent short circuiting between the anode and the cathode. The porous separator typically consists of a single-ply or multi-ply sheet of a microporous polymer such as polyethylene, polypropylene, or a combination thereof. The pore size of the porous separator is sufficiently large to permit transport of ions, but small enough to prevent contact of the anode and cathode either directly or from particle penetration or dendrites which can form on the anode and cathode.

In one embodiment, the electrochemical cell is a lithium ion battery. Suitable anode materials for a lithium ion battery include, but are not limited to, lithium metal, lithiated carbon, or a lithium alloy. Suitable cathode materials for a lithium ion battery include, but are not limited to, electroactive transition metal oxides comprising lithium, such as $LiCoO_2$, $LiNiO_2$, $LiMn_2O_4$, or $LiV_3O_8$. Electrolyte compositions suitable for use in lithium ion batteries are described above.

The electrochemical cells disclosed herein may be used as a power source in various electronic articles such as computers, power tools, automobiles, and telecommunication devices.

EXAMPLES

The present invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "s" means second(s), "mL" means milliliter(s), "μL" means microliter(s), "g" means gram(s), "mg" means milligram(s), "μg" means microgram(s), "mol" means mole(s), "mmol" means millimole(s), "cm" means centimeter(s), "mm" means millimeter(s), "mbar" means millibar(s), "Pa" means pascal(s), "mtorr" means millitorr, "mbar" means millibar, "M" means molar concentration, "wt %" means percent by weight, "Hz" means hertz, "mS" means millisiemen(s), "mA" mean milliamp(s), "V" means volt(s), "mV" means millivolt(s), "$^1$H NMR" means proton nuclear magnetic resonance spectroscopy, "$^{19}$F NMR" means fluorine 19 nuclear magnetic resonance spectroscopy.

All reagents used in the following examples were obtained from Sigma-Aldrich (Milwaukee, Wis.), unless otherwise noted.

Reagent Preparation

Preparation of Methyl 2,2,3,3-Tetrafluoropropyl Carbonate (FS-C)

Methyl chloroformate (130 mL, 159 g, 1.68 mol) was added slowly over a period of 3 h to a solution of 2,2,3,3-tetrafluoropropanol (132 g, 1.00 mol) in pyridine (300 mL, anhydrous) at −10° C. to 0° C. with magnetic stirring. The reaction mixture was stirred at room temperature overnight. Then, the reaction mixture was mixed with 5% HCl (500 mL) and approximately 50 g of ice, and the resulting mixture was extracted three times with 300 mL portions of ether. The combined organic layer was washed three times with 100 mL portions of 5% HCl, followed by two washes with 100 mL portions of 5% sodium carbonate. The organic phase was then dried over anhydrous sodium sulfate. Ether was removed by rotary evaporation. The crude product (approximately 200 g) was distilled, yielding 166 g (87% yield) of pure methyl 2,2,3,3-tetrafluoropropyl carbonate, also referred to herein as "FS-C". NMR analysis data were consistent with the literature values (U.S. Pat. No. 5,659,062).

Preparation of Methyl 2,2,2-Trifluoroethyl Carbonate (FS-D)

In a dry box, methyl chloroformate (219 mL, 268 g, 2.84 mol) was added slowly to a solution containing 2,2,2-trifluoroethanol (233.5 g, 2.335 mol), pyridine (225 g), and dichloromethane (1.2 L, anhydrous) at −10° C. to 30° C. (the dichloromethane was cooled in a freezer before use), with magnetic stirring. The reaction mixture was stirred at room temperature in the dry box overnight. The reaction mixture was then taken out of the dry box, and was washed with 5% HCl (300 mL), followed by 3 washes with 50 mL portions of 5% HCl, one wash with 5% sodium carbonate (100 mL), and 2 washes with 100 mL portions of brine. The organic phase was then dried over anhydrous sodium sulfate. Dichloromethane was removed by rotary evaporation. The residue liquid was distilled with a spinner band column, yielding 185.4 g (46% yield) of pure methyl 2,2,2-trifluoroethyl carbonate, also referred to herein as "FS-D". NMR analysis data were consistent with literature values (U.S. Pat. No. 5,659,062).

Example 1

Synthesis of 2-(Methylsulfonyl)ethyl 2,2,2-Trifluoroacetate (FS-A)

Under nitrogen, trifluoroacetic anhydride (16.4 g, 78.0 mmol, 10.9 mL) was added dropwise to 2-methylsulfonyl ethanol (8.07 g, 65.0 mmol) in an oven-dried 50-mL round-bottom flask. During the addition the contents of the flask were mixed using magnetic stirring and the flask was cooled in a water bath at room temperature. After the addition was completed, the reaction mixture was stirred at room temperature for one more hour. Then, the 2-(methylsulfonyl)ethyl 2,2,2-trifluoroacetate product, also referred to herein as "FS- A", was purified by vacuum distillation and collected at 2 mbar (200 Pa), 122.0-123.0° C. (12.0 g, 84% yield).

The final product was analyzed by $^1$H NMR and $^{19}$F NMR.

$^1$H NMR (CDCl3): δ 4.81 (t, 2H, J=5.7 Hz), 3.43 (t, 2H, J=5.7 Hz), 3.01 (s, 3H). $^{19}$F NMR (CDCl3): δ −74.8 (s, 3F).

Example 2

Synthesis of 2-(Methylsulfonyl)ethyl 2,2,-Difluoroacetate (FS-B)

In a dry box, 2-methylsulfonyl ethanol (6.8 g, 55 mol) in dichloromethane (20 mL) was added to a solution of difluoroacetic anhydride, obtained from SynQuest, Alachua, Fla., (13.0 g, 68 mmol) in dichloromethane, obtained from EMD, Gibbstown, N.J., (20 mL) at a temperature of 0 to 18° C. The resulting mixture was stirred for 3 h. After this time, the reaction was determined to be completed by NMR. The volatile solvent was removed by rotoevaporation. Then, the 2-(methylsulfonyl)ethyl 2,2-difluoroacetate product, also referred to herein as "FS-B" was purified by vacuum distillation and collected at 60 mtorr (8.0 Pa), 100° C. (10 g, 90% yield). The final product was analyzed by $^1$H NMR and $^{19}$F NMR.

$^1$H NMR (CDCl3): δ 6.01 (t, 1H, J=53.0 Hz), 4.73 (t, 2H, J=5.7 Hz), 3.43 (t, 2H, J=5.7 Hz), 3.01 (s, 3H). $^{19}$F NMR (CDCl3): δ −127.2 (d, 2F, J=53.0 Hz).

Examples 3-9

Preparation of Nonaqueous Electrolyte Solutions

These examples describe the preparation of nonaqueous electrolyte solutions containing lithium hexafluorophosphate in two-component solvents.

The nonaqueous electrolyte solutions were prepared by weighing predetermined amounts of the components into vials in a dry box. The lithium hexafluorophosphate (LiPF$_6$) (battery grade, Stella Chemifa Corp., Tokyo, Japan) was weighed into each vial to give a final concentration of 0.5 M. Then, the first electrolyte solvent and the second electrolyte solvent were weighed into each vial to give the desired weight percent (wt %) of each component. The compositions of the electrolyte solvents are summarized in Table 1. The electrolyte solvents ethyl methyl carbonate (EMC) and ethylene carbonate (EC) were battery grade, obtained from Ferro Corp. (Cleveland, Ohio).

TABLE 1

Compositions of Nonaqueous Electrolyte Solutions

| Example | LiPF$_6$ (M) | First Electrolyte Solvent (wt %) | Second Electrolyte Solvent (wt %) |
|---|---|---|---|
| 3 Comparative | 1.0 | EMC (63%) | EC (37%) |
| 4 Comparative | 0.5 | FS-C (70%) | EC (30%) |
| 5 Comparative | 0.5 | FS-D (70%) | EC (30%) |
| 6 | 0.5 | FS-C (70%) | FS-A[a] (30%) |
| 7 | 0.5 | FS-C (70%) | FS-B[b] (30%) |
| 8 | 0.5 | FS-D (70%) | FS-A[a] (30%) |
| 9 | 0.5 | FS-D (70%) | FS-B[b] (30%) |

[a]Prepared as described in Example 1.
[b]Prepared as described in Example 2.

Example 10

Electrolyte Ionic Conductivity

The electrical conductivity of the nonaqueous electrolyte solutions described in Examples 3-9 was measured using ac impedance spectroscopy over the frequency range of 0.1 to 1,000,000 Hz. The impedance results were fit with an equivalent circuit model to yield the dc resistance.

An electrical probe containing two wires was first calibrated over the conductivity range of 10 to 100,000 Hz using standard aqueous solutions of sodium chloride. Then, the electrical probe was placed in the nonaqueous electrolyte solution to be measured. Ionic conductivity measurements were recorded at temperatures of 20-28° C. in a dry box.

Results were extrapolated to 25° C. using the temperature dependence of 2.0%/° C. The results summarized in Table 2 are reported at 25° C.

TABLE 2

Ionic Conductivity of Nonaqueous Electrolyte Solutions at 25° C.

| Nonaqueous Electrolyte Solution | Ionic Conductivity (mS/cm) |
|---|---|
| Example 3 Comparative | 9.34 |
| Example 4 Comparative | 2.81 |
| Example 5 Comparative | 4.39 |
| Example 6 | 0.28 |
| Example 7 | 0.19 |
| Example 8 | 0.27 |
| Example 9 | 0.41 |

Example 11

Electrochemical Stability to Oxidation

Measurements of electrochemical stability were carried out in a three terminal electrochemical cell with a salt bridge connecting the sample chamber to a chamber containing a reference electrode.

Measurements were made using 1.6 mm diameter platinum working electrodes with a platinum wire counter electrode, all located in the sample chamber. Approximately, 0.6 mL of a nonaqueous electrolyte solution, as described in Examples 3-9, was added to the sample chamber for the measurement. The reference electrode was a silver wire in a solution containing 0.01 M LiPF$_6$ in propylene carbonate. The reference electrode chamber was connected to the sample chamber via a salt bridge containing 1.0 M LiPF$_6$ solution in propylene carbonate. A Vycor® porous glass frit (BASi, West Lafayette, Ind.) was used to separate the salt bridge from the sample chamber and the reference electrode chamber.

The electrochemical measurements were made using a PAR 273A potentiostat (AMETEK Princeton Applied Research, Oak Ridge, Tenn.), which was controlled by CorrWare® software (Scribner Associates Inc., Southern Pines, N.C.) using the following procedure. Wires were attached to the electrodes and the open circuit potential was allowed to stabilize. Then, the potentiostat potential applied to the working electrode was set to the open circuit potential. The applied potential was ramped at a rate of 10 mV/s from the open circuit potential to a potential of 4.0 V versus the Ag/Ag$^+$ reference electrode and the current was recorded as a function of potential.

The results were compared at a current density of 1.0 mA/cm$^2$ and are summarized in Table 3.

TABLE 3

Electrochemical Stability of Electrolytes to Oxidation

| Nonaqueous Electrolyte Solution | Potential of Pt Electrode versus Reference Electrode (V) at a Current Density of 1.0 mA/cm$^2$ |
| --- | --- |
| Example 3 Comparative | 2.25 |
| Example 4 Comparative | 2.97 |
| Example 5 Comparative | 2.89 |
| Example 6 | 3.11 |
| Example 7 | 3.08 |
| Example 8 | 3.15 |
| Example 9 | 3.05 |

The current results from electrochemical oxidation on the cathode and a high cathode potential for a current density of 1.0 mA/cm$^2$ are indicative of an electrolyte composition that is stable at higher potentials. Specifically, the electrolyte compositions containing the fluorinated electrolyte solvents of the invention (Examples 6-9) are oxidized at higher potentials than those containing EC (Examples 3-5 Comparative).

Example 12

Electrolyte Performance in Lithium Ion Batteries

Electrochemical cells (2032 coin cells) were prepared with graphite/copper anodes (Pionics Co., Ltd., Shiga, Japan), LiCoO$_2$/copper cathodes (Pionics Co., Ltd.) and a polyethylene/polypropylene separator (Celgard® battery separator, Celgard LLC., Charlotte, N.C.). The nominal cathode loading was 1.5 mA-h/cm$^2$ based on the initial discharge capacity for cycling with a standard battery electrolyte (Example 3) between 2.7 and 4.2 V at a current of 0.25 mA.

Circular pieces of the separator were cut with a ¾ inch arch punch and the pieces were transferred to a glovebox. Circular sections of cathodes were cut with a 9/16 inch arch punch. The resulting cathodes had a nominal cathode loading of 2.5 mA-h based on conversion of LiCoO$_2$ to Li$_{0.5}$CoO$_2$. Circular sections of the anodes were cut with a ⅝ inch arch punch. The pre-cut cathode and anode sections were heated to 90° C. for 12 h under vacuum in an antechamber, and then transferred to a glovebox.

The coin cells consisted of coin cell cases (SUS316L), spacer disks, wave springs, and caps, and a polypropylene casket, all obtained from Hohsen Corp. (Osaka, Japan). The coin cell components were sonicated in ultra-high purity water with detergent for one hour, rinsed with ultra-high purity water for 60 min, and then dried at 90° C. under house vacuum. The cleaned coin cell components were transferred to a glovebox.

A circular cathode section was placed in the coin cell case and 4 drops (about 0.2 mL) of the nonaqueous electrolyte solution to be tested, as described in Examples 3-9, were added. A circular anode section was then placed on the wetted cathode. The circular anode section was placed on top of the separator. The spacer disk was set on the anode and all layers were aligned in the center of the coin cell case. The wave spring was set on top of the spacer disk and aligned. The gasket was attached to the cap and the gasket-cap assembly was set on top of the wave spring. The assembly was placed in a coin cell battery crimper (Hohsen Corp.) and pressure was applied to seal the coin cell.

The coin cell batteries were tested in an Arbin battery tester (Arbin Instruments, College Station, Tex.). The coin cell batteries were charged to 4.2 V at a constant current of 0.25 mA, held at open circuit for 10 min, and then discharged to 2.7 V at a constant current of 0.25 mA. The coin cell batteries were next held at open circuit for 10 min and then charged again to 4.2 V at a constant current of 0.25 mA. This process was repeated for 5 charge-discharge cycles. The discharge capacity was recorded by integrating the current during the discharge part of the cycle. The discharge capacity is provided as a function of the cycle number in Table 4 for the electrolyte compositions of Comparative Example 3 and Examples 8 and 9. These coin cell batteries demonstrate the utility of the compositions of the invention in lithium ion secondary batteries.

TABLE 4

Discharge Capacity versus Cycle Number for Electrolytes

| | Discharge Capacity (mA-h) | | |
| --- | --- | --- | --- |
| Cycle Number | Example 3, Comparative | Example 8 | Example 9 |
| 1 | 2.515 | 1.916 | 1.980 |
| 2 | 2.493 | 1.829 | 1.852 |
| 3 | 2.477 | 1.710 | 1.773 |
| 4 | 2.465 | 1.652 | 1.703 |
| 5 | 2.454 | 1.602 | 1.685 |

What is claimed is:

1. A process for forming a product compound as represented by the structure of the following formula

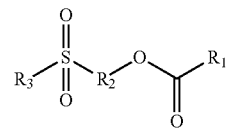

wherein R$_1$ is C$_1$ to C$_4$ fluoroalkyl; R$_2$ is C$_1$ to C$_6$ alkylene radical, optionally substituted with one or more ether oxygens; and R$_3$ is C$_1$ to C$_6$ alkyl, optionally substituted with one or more ether oxygens, comprising the step of: combining, optionally in a solvent, a)

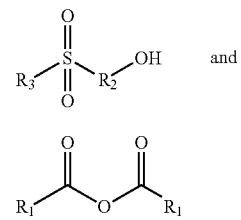

b)

wherein R$_1$, R$_2$ and R$_3$ are as set forth above.

2. The process according to claim 1 wherein each R$_1$ is CF$_3$, R$_2$ is CH$_2$CH$_2$, and R$_3$ is CH$_3$.

3. The process according to claim 1 wherein each R$_1$ is CF$_2$H, R$_2$ is CH$_2$CH$_2$, and R$_3$ is CH$_3$.

4. The process according to claim 1 wherein the optional solvent is selected from the group consisting of dichloromethane, chloroform, ether, and tetrahydrofuran.

5. The process according to claim 1 further comprising admixing the product with an electrolyte salt, and optionally with a solvent component, to form an electrolyte composition.

6. The process according to claim 5 further comprising incorporating the electrolyte composition formed thereby into an electrochemical cell.

7. A composition comprising:
(a) a compound represented by the structure of the following formula:

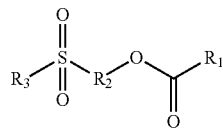

wherein $R_1$ is $C_1$ to $C_4$ fluoroalkyl; $R_2$ is $C_1$ to $C_6$ alkylene radical, optionally substituted with one or more ether oxygens; and $R_3$ is $C_1$ to $C_6$ alkyl, optionally substituted with one or more ether oxygens; and
(b) at least one electrolyte salt.

8. The composition according to claim 7 further comprising at least one solvent component selected from the group consisting of ethyl methyl carbonate, dimethyl carbonate, diethyl carbonate, ethylene carbonate, propylene carbonate, vinylethylene carbonate, fluoroethylene carbonate, 2,2,2-trifluoroethyl carbonate, and methyl 2,2,3,3-tetrafluoropropyl carbonate.

9. The composition according to claim 1 wherein the electrolyte salt is selected from the group consisting of lithium hexafluorophosphate, lithium bis(trifluoromethanesulfonyl)imide, lithium bis(perfluoroethanesulfonyl)imide, lithium tetrafluoroborate, lithium perchlorate, lithium hexafluoroarsenate, lithium trifluoromethanesulfonate, lithium tris(trifluoromethanesulfonyl)methide, lithium bis(oxalato)borate, $Li_2B_{12}F_{12-x}H_x$ where x is equal to 0 to 8, and mixtures of lithium fluoride and $B(OC_6F_5)_3$.

10. The composition according to claim 9 wherein the electrolyte salt is lithium hexafluorophosphate.

11. The composition according to claim 7 wherein $R_1$ is $CF_3$, $R_2$ is $CH_2CH_2$, and $R_3$ is $CH_3$.

12. The composition according to claim 7 wherein $R_1$ is $CF_2H$, $R_2$ is $CH_2CH_2$, and $R_3$ is $CH_3$.

13. An electrochemical cell comprising:
(a) a housing;
(b) an anode and a cathode disposed in said housing and in ionically conductive contact with one another;
(c) an electrolyte composition disposed in said housing and providing an ionically conductive pathway between said anode and said cathode, wherein the electrolyte composition comprises a composition represented by the structure:

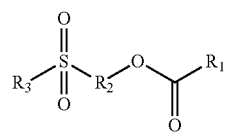

and at least one electrolyte salt, wherein $R_1$ is $C_1$ to $C_4$ fluoroalkyl; $R_2$ is $C_1$ to $C_6$ alkylene radical, optionally substituted with one or more ether oxygens; and $R_3$ is $C_1$ to $C_6$ alkyl, optionally substituted with one or more ether oxygens; and
(d) a porous separator between said anode and said cathode.

14. The electrochemical cell according to claim 13 wherein $R_1$ is $CF_3$, $R_2$ is $CH_2CH_2$, and $R_3$ is $CH_3$.

15. The electrochemical cell according to claim 13 wherein $R_1$ is $CF_2H$, $R_2$ is $CH_2CH_2$, and $R_3$ is $CH_3$.

16. The electrochemical cell according to claim 13 wherein said electrochemical cell is a lithium ion battery.

17. An article comprising the electrochemical cell according to claim 13.

* * * * *